Figure 1:
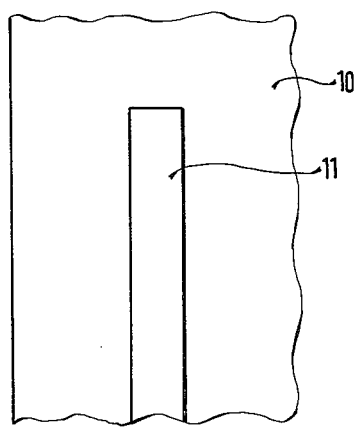

United States Patent [19]

Friese et al.

[11] 4,280,890
[45] Jul. 28, 1981

[54] ELECTROCHEMICAL SENSOR FOR OXYGEN CONCENTRATION DETERMINATION IN GASES AND METHOD OF MAKING THE SAME

[75] Inventors: Karl-Hermann Friese, Leonberg; Wolf-Dieter Haecker, Asperg; Bürkhard Pfeiffer, Ditzingen, all of Fed. Rep. of Germany

[73] Assignee: Robert Bosch GmbH, Stuttgart, Fed. Rep. of Germany

[21] Appl. No.: 130,453

[22] Filed: Mar. 14, 1980

[30] Foreign Application Priority Data

Mar. 21, 1979 [DE] Fed. Rep. of Germany ....... 2911042

[51] Int. Cl.³ .................. B05D 1/34; G01N 27/58
[52] U.S. Cl. ..................... 204/195 S; 427/123; 427/125; 427/426
[58] Field of Search .................. 204/195 S, 1 S; 427/426, 123, 125

[56] References Cited

U.S. PATENT DOCUMENTS

| | | | |
|---|---|---|---|
| 3,843,400 | 10/1974 | Radford et al. | 204/195 S X |
| 3,978,006 | 8/1976 | Topp et al. | 204/195 S X |
| 4,021,326 | 5/1977 | Pollner et al. | 204/195 S |
| 4,080,276 | 3/1978 | Bode | 204/195 S |
| 4,097,353 | 6/1978 | Kishida et al. | 204/195 S |
| 4,170,530 | 10/1979 | Watanabe et al. | 204/195 S |

FOREIGN PATENT DOCUMENTS 2631721 12/1977 Fed. Rep. of Germany .

Primary Examiner—G. L. Kaplan
Attorney, Agent, or Firm—Frishauf, Holtz, Goodman & Woodward

[57] ABSTRACT

To decrease the quantity of catalytically active noble metal used in a Cermet (ceramic-metal) electrode, particularly one containing platinum, the electrode has a non-uniform noble metal concentration, with respect to its cross section, so that the outer region thereof consists essentially only of ceramic material, protecting the softer noble metal which is subject to erosion, and permitting a higher concentration of noble metal close to the solid electrolyte body where it is most needed. This type of electrode can be applied, for example, by concurrent spraying of an aqueous suspension of noble metal-and-ceramic from one nozzle, and a suspension of only ceramic from another nozzle, and varying the throughput through the two nozzles, first only spraying the metal-ceramic mixture and then starting the ceramic-only suspension while decreasing the mixture suspension until only ceramic material is sprayed; in accordance with another method, the solid electrolyte body can, for example, be dipped in sequential suspensions or have sequential suspensions applied thereto by dripping-on, painting-on, or the like. The electrode and the solid electrolyte body, for example zirconium dioxide, are then sintered.

24 Claims, 3 Drawing Figures

4,280,890

ELECTROCHEMICAL SENSOR FOR OXYGEN CONCENTRATION DETERMINATION IN GASES AND METHOD OF MAKING THE SAME

The present invention relates to an electrochemical sensor to determine the concentration of oxygen in gases, and more particularly in combustion gases, especially in the exhaust gases from internal combustion engines, for example of the automotive type, and to methods of its manufacture.

BACKGROUND AND PRIOR ART

It has previously been proposed to construct an electrochemical sensor by applying an electrode layer on a solid electrolyte body by sintering. This electrode layer is applied at least at the side of the solid electrolyte body exposed to the gas to be tested. To provide protection to the electrode, the electrode layer is formed of a mixture of a noble metal powder and a ceramic powder. The ceramic powder typically is of similar composition as that of the solid electrolyte body (see German published patent application DE-AS No. 26 31 721). Such sensors require a considerable amount of noble metal, typically platinum, and in the sensors as proposed, the platinum content may be between 30–50% (by volume) in order to provide sufficient electrical conductivity to the electrodes-ceramic composite layer, so that a suitable output voltage can be derived from the sensor.

The price of noble metals continues to rise and, in mass production items, it is desirable to reduce the noble metal content as much as possible so that the costs of such high-volume articles can be kept reasonable and reduced. A sensor which has an electrode layer with a high content of noble metal, further, is not as resistant to the corrosive influences of hot combustion gases as desirable. Platinum is comparatively soft and is gradually eroded, which causes difficulties in the cohesion of the overall electrode layer.

THE INVENTION

It is an object to provide an electrochemical sensor in which the content of noble metal in the electrode is reduced, and which is more resistant to the corrosive influence of hot combustion gases than previously proposed sensors.

Briefly, in accordance with the invention, the combination metal-ceramic electrode on a solid ion conductive body is so arranged that the noble metal content in the electrode which is exposed to the gas to be measured increases in the direction towards the solid electrolyte body from the outside thereof, so that the ceramic material of the composite electrode itself forms a protection for the soft platinum content where the exposure to the gas is most severe, thus permitting use of a lesser quantity of noble metal while still providing sufficient electrical conductivity and catalytic effect thereof.

The sensor has the advantage that the electrode layer, when constructed as proposed, can be made with material in which the expensive noble metal is a comparatively small percentage. A high content of noble metal, for example over 30% (by volume), is only necessary in a base layer immediately adjacent the solid electrolyte body. Such a base layer may have a thickness of from between 2 to 5 $\mu$m. In the surface which is exposed to the gas to be tested, only very little or practically no platinum is contained, so that erosion of platinum is avoided and thus the electrode layer will retain its strength and cohesion over a long period of time. Continuously varying the content of platinum within the electrode, that is, continuously changing the composition of the composite electrode as the distance from the outside surface to the solid electrolyte body increases ensures good mechanical strength and resistance to temperature shocks. Thinner electrode layers are possible, for example having thicknesses in the range of from between 0.020 to 0.1 mm. Although the thickness of the layer may be greater, the above range, and particularly within the lower region thereof, is preferred.

In accordance with a feature of the invention, the sensor can be made simply by applying the electrode which is exposed to the gas to be tested or measured in the form of two suspensions, one suspension being a mixture of a catalytically active noble metal powder, such as platinum, and a powder of the ceramic material; and the other suspension being only the powder of the ceramic material. The first suspension—that is, the mixture of noble metal and ceramic powder—is first sprayed on the solid electrolyte support or base body and then is sprayed on more and more of the second suspension while decreasing the first so that, in the end, only the second suspension is applied. The thus applied electrode and the base body are then sintered together.

DRAWING

Figure 2:
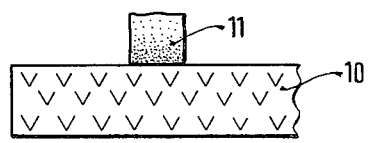
Figure 3:
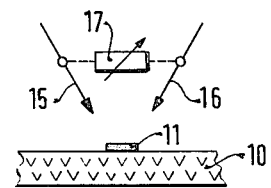

FIG. 1 is a plan view, in highly schematic representation, of an electrode on a solid electrolyte body. The geometric arrangement of the electrode on the solid electrolyte body does not form part of the present invention;

FIG. 2 is a highly schematic sectional view through the solid electrolyte body with the electrode thereon, in which the elements are not to scale, and the electrode is shown stippled with increasing stippling density towards the solid electrolyte body to visualize the higher degree of concentration of noble metal; and FIG. 3 is a highly schematic view illustrating an apparatus to carry out the method of application of the electrode.

The sensor comprises a solid electrolyte body of stabilized zirconium dioxide 10. This body may be in the form of a tube, closed at one end, to which the electrode 11 is applied. Reference is made to U.S. Pat. No. 3,798,006, Topp and Friese, assigned to the assignee of this application, which illustrates an example of the overall structure. The electrode 11, in accordance with the present invention, is a mixture of platinum powder and zirconium dioxide in which the quantity of platinum increases towards the surface area of the zirconium body 10, as schematically indicated in FIG. 2.

The electrode, in accordance with a feature of the invention, is applied as follows: The ion conductive solid electrolyte body 10 is presintered up to a presintering temperature, so that the presintering process leads to a relatively strong but still porous electrolyte body 10. Two nozzles 15, 16, which can be similar to nozzles used in glazing, are positioned to direct a stream of a suspension towards a predetermined zone of the solid electrolyte body 10. If the electrolyte body 10 is a tube, to be covered throughout the circumference, the tube can be placed on a mandrel and rotated while the nozzles 15, 16 spray the respective fluid thereon. One of the nozzles, for example nozzle 15, has supplied thereto an aqueous suspension comprising 50% platinum and 50% presintered pulverized ceramic (percentages by volume). The pulverized ceramic consists of 92 mol-% $ZrO_2$ and 8 mol-% $Y_2O_3$. The second nozzle, for example nozzle 16, has applied thereto an aqueous suspension which consists only of the presintered mixture of powder of zirconium dioxide and yttrium oxide, without platinum. The two suspensions are then sprayed on the body, for example while the body is rotating, in such a manner that first only the suspension from nozzle 15 and containing the platinum is applied thereon. Thereafter, the flow or throughput of the platinum-containing suspension is decreased and a controlled valve is opened to permit flow of platinum-free suspension from nozzle 16. Preferably, the decrease in flow nozzle 15 is balanced by the increase in flow from nozzle 16 so that the overall application of suspension to the body 10—per unit time—will remain the same. The suspensions are sprayed on the base body 10 until an electrode layer 11 is built up which has a layer thickness of between 20 to 100 $\mu$m. After the layer is applied, it is dried at a temperature of about 100° C. The electrode can be connected to an external circuit by a conductive track which has been applied before the suspensions were sprayed on the surface region of body 10 which is exposed to the gas to be tested. The conductive track may consist, for example, of the same mixture as the platinum-containing suspension, but of much smaller extent—for example, rather than covering a major portion of the surface area of the electrode 10, the conductor may be in the form of a narrow strip. At the time the conductive track was applied, a counter electrode for a reference gas can have been applied at the interior of the solid electrolyte tube, that is, on the obverse side of the body 10 (FIG. 2).

After the suspensions have dried, the solid electrolyte body with the applied electrode layer is sintered at a temperature of about 1500° C.

A similar process can be used with a fully sintered solid electrolyte base body. If the base body is fully sintered, the nozzle 15 preferably is supplied with a suspension containing 50% (by volume) platinum and 50% (by volume) pulverized barium-aluminum-silicate glass. The other nozzle, that is, nozzle 16, will have a suspension of only the glass powder applied therethrough. Sintering then will be carried out at about 1100° C.

The degree of suspension, that is, the water content, can be easily determined, and will depend on the apparatus used to apply the suspensions and drying arrangements. A suspension of 10 to 50%, preferably about 25% solid material to 90 to 50%, preferably 35% water (by volume) is suitable for the suspension through nozzle 15 and also for the suspension for nozzle 16. It is advantageous to add a small amount of organic binder to the suspensions, such as polyvinylalcohol or others, preferably up to 2% by weight in relation to the solid material. Even small amounts of anti-foam additives are advantageous, e.g. 0.01% by weight in relation to the suspensions. Controller 17 controls the relative flow through nozzles 15,16.

It is not necessary that the respective suspensions are applied simultaneously. It is also possible to operate in a sequential mode. First, that suspension is applied to the base body 10 which has the highest platinum content and thereafter a suspension is connected to the respective nozzle which has a lesser platinum content and, eventually, one which has none at all. It is also possible to first apply a suspension with platinum, and then a suspension which contains none. In sequential operations, it is desirable to apply the subsequent layer on a previously applied layer when the previously applied layer is still wet. Application can be, as previously described, by spraying-on, but may also be applied by dipping on or by immersion of the solid electrolyte body into suspensions containing lesser or no platinum.

A solid electrolyte body first has a suspension of 50% (by volume) platinum and 50% (by volume) of the above referred-to powder mixture of 92 mol-% zirconium dioxide and 8 mol-% yttrium oxide applied thereto. The application can be, for example, by dipping the end portion of a closed tube, for example as illustrated in the aforementioned U.S. Pat. No. 3,798,006, into the suspension. Upon removal, and letting the suspension drip off, and while it is still damp or moist, the previously dipped zone is then dipped into a second suspension to apply a second layer; the second suspension has 25% (volume) platinum and 75% (volume) of the above referred-to mixture of powder; after letting this suspension drip off, and while the surface is still moist, a third suspension consisting only of the powder mixture is applied. After any excess has dripped off, the entire unit is sintered, for example at between about 1400°–1700° C., preferably about 1500° C.

The electrode itself preferably contains platinum or a platinum alloy such as platinum-rhodium; the ceramic need not be zirconium dioxide, but may also include magnesium spinel, aluminum oxide, as well as partially or fully stabilized zirconium dioxide, titanium dioxide, or high-melting point glasses such as barium-aluminum-silicate glasses. The noble steel is needed in order to catalyze the gas equilibrium. In addition, and particularly in the region of the conductive track, the electrode may further contain other conductive materials which are not catalytically active, or essentially catalytically inactive. For example, the electrode may contain palladium, gold, nickel, nickel alloys such as iron-chromium-nickel alloys, electron conductive oxides such as Perowskite, doped La-Co-oxide, or spinels, for example $Ni_xFe_{3-x}O_4$ wherein x has a value of 0 or 1, or values therebetween, or carbide, or SiC.

We claim:

1. Electrochemical sensor for determination of the concentration of oxygen in gases, particularly in gases resulting from combustion processes, such as exhaust gases from internal combustion engines, having an ion conductive solid electrolyte body (10) and an electrode (11) applied to a surface thereof, adapted to be exposed to the gases, said electrode comprising a mixture of a ceramic and a noble metal which catalyzes the thermodynamic equilibrium of the gases with respect to a reference, wherein, in accordance with the invention, the concentration of noble metal in the electrode is non-uniform, in cross section, and decreases in the direction away from the surface of the solid electrolyte body (10) towards the surface of the electrode exposed to the gases.

2. Sensor according to claim 1, wherein the concentration of noble metal decreases continuously.

3. Sensor according to claim 1, wherein the noble metal comprises at least one of the materials selected from the group consisting of platinum and platinum alloy;

and the ceramic comprises at least one of the materials selected from the group consisting of magnesium spinel, aluminum oxide, partially stabilized zirconium dioxide, fully stabilized zirconium dioxide, titanium dioxide, and a high melting glass.

4. Sensor according to claim 1, wherein the electrode further includes electron conductive metals which are essentially catalytically inactive.

5. Sensor according to claim 4, wherein the electrode comprises at least one material of the group consisting of: palladium, gold, nickel, an iron-chromium-nickel alloy; doped La-Co-oxide; Perowskite; $Ni_xFe_{3-x}O_4$ wherein x has a value of 0 or 1 or any value inbetween;

6. Sensor according to claim 5, wherein the noble metal comprises at least one of the materials of the group consisting of platinum and platinum alloy;

and the ceramic comprises at least one of the materials selected from the group consisting of magnesium spinel, aluminum oxide, partially stabilized zirconium dioxide, fully stabilized zirconium dioxide, titanium dioxide, and a high melting glass.

7. Sensor according to claim 5 wherein the carbide is SiC.

8. Sensor according to claim 4, wherein the electron conductive metal comprises a nickel alloy.

9. Sensor according to claim 4, wherein the electrode comprises an electron conductive oxide.

10. Sensor according to claim 1, wherein the noble metal comprises at least one of the materials selected from the group consisting of platinum and platinum alloy.

11. Sensor according to claim 1, wherein the noble metal comprises platinum-rhodium.

12. Sensor according to claim 1 or 5 or 6 or 10 or 11 or 8, wherein the ceramic comprises at least one of the materials selected from the group consisting of magnesium spinel, aluminum oxide, partially stabilized zirconium dioxide, fully stabilized zirconium dioxide, titanium dioxide, a high-melting glass.

13. Sensor according to claim 1 or 5 or 6 or 10 or 11 or 8, wherein the ceramic material comprises barium-aluminum-silicate glass.

14. Method of manufacturing an electrochemical sensor for the determination of oxygen concentration in gases, particularly in gases resulting from a combustion process, such as exhaust gases from an internal combustion engine, having an ion conductive solid electrolyte body (10);
and an electrode applied to a surface thereof adapted to be exposed to the gases, and which is composed of a mixture of a ceramic and a noble metal which catalyzes the thermodynamic equilibrium of the gases with respect to a reference, and which is characterized in that the concentration of nobel metal, in cross section, is non-uniform and decreases in the direction away from the surface of the solid electrolyte body (10) towards the surface exposed to the gases, said method comprising the steps of providing a first suspension comprising an aqueous mixture of the noble metal powder, and a powder of a ceramic material;
providing a second aqueous suspension of the powder of the ceramic material alone;
applying said first suspension to the surface of the solid electrolyte material where the electrode is to be applied and decreasing the rate of application of said first suspension while beginning to apply the second suspension at an increasing rate until the requisite electrode layer thickness is reached.

15. Method according to claim 14, wherein the change in the rate of application of the first suspension, and of the second suspension, respectively, is selected such that, when the requisite thickness of the electrode is reached, application of the first suspension has terminated.

16. Method according to claim 15, wherein the change in the rate of application is uniformly continuous.

17. Method according to claim 15, wherein the change in the rate of application is in steps.

18. Method according to claim 15, wherein the application step comprises applying said suspensions through spray nozzles (14, 15).

19. Method according to claim 14, wherein said first suspension comprises an aqueous mixture of 50% platinum and 50% presintered pulverized ceramic (both by volume) comprising 92 mol-% $ZrO_2$ and 8 mol-% $Y_2O_3$;

said second suspension comprises a presintered pulverized aqueous mixture of 92 mol-% $ZrO_2$ and 8 mol-% $Y_2O_3$;
said application step comprises spraying said mixtures on the surface of the solid electrolyte body;
and further comprising the step of sintering the solid electrolyte body, with the applied mixtures, at a temperature of between 1400° to 1700° C.

20. Method according to claim 19, wherein the spraying step comprises first only spraying the first suspension onto the solid electrolyte body, and then continuously decreasing the quantity of the first suspension being sprayed on the solid electrolyte body while continuously increasing the quantity of the second suspension, and finally spraying only said second suspension;

and wherein said solid electrolyte body (10) is partially sintered or presintered, and said sintering step comprises finally sintering said solid electrolyte body.

21. Method according to claim 14, wherein said solid electrolyte body is completely sintered;

and said first suspension comprises a mixture of (by volume) 50% platinum and 50% pulverized barium-aluminum-silicate glass;
and further including the step of sintering the solid electrolyte body with the suspensions applied at a temperature of about 1100° C.

22. Method according to claim 21, wherein the spraying step comprises first only spraying the first suspension onto the solid electrolyte body, and then continuously decreasing the quantity of the first suspension being sprayed on the solid electrolyte body while continuously increasing the quantity of the second suspension, and finally spraying only said second suspension.

23. Method according to claim 14, wherein said application step comprises first applying a first suspension having a first ratio of concentration of catalytically active noble metal and ceramic material;

before applying said second suspension applying at least one intermediate layer of a third suspension having a lesser concentration of catalytically active noble metal powder, and a higher content of ceramic powder therein;
and further including the step of sintering said layers of suspensions and the solid electrolyte body.

24. Method according to claim 23, wherein the second suspension is devoid of catalytically active noble metal.

* * * * *